United States Patent
Lubda et al.

(10) Patent No.: US 11,510,986 B2
(45) Date of Patent: Nov. 29, 2022

(54) HOT MELT EXTRUSION COMPOSITION USING DIRECT COMPRESSIBLE EXCIPIENT AS PLASTICIZER

(71) Applicant: MERCK PATENT GMBH, Darmstadt (DE)

(72) Inventors: Dieter Lubda, Bensheim (DE); Mengyao Zheng, Bensheim (DE); Alessandro Giuseppe Elia, Darmstadt (DE); Nicole Di Gallo, Bensheim (DE)

(73) Assignee: MERCK PATENT GMBH, Darmstadt (DE)

( * ) Notice: Subject to any disclaimer, the term of this patent is extended or adjusted under 35 U.S.C. 154(b) by 578 days.

(21) Appl. No.: 16/301,327

(22) PCT Filed: May 10, 2017

(86) PCT No.: PCT/EP2017/061126
§ 371 (c)(1),
(2) Date: Nov. 13, 2018

(87) PCT Pub. No.: WO2017/194576
PCT Pub. Date: Nov. 16, 2017

(65) Prior Publication Data
US 2020/0254098 A1   Aug. 13, 2020

(30) Foreign Application Priority Data
May 13, 2016 (EP) ..................... 16169693

(51) Int. Cl.
| | | |
|---|---|---|
| *A61K 31/405* | (2006.01) | |
| *A61K 47/26* | (2006.01) | |
| *A61K 9/14* | (2006.01) | |
| *C08K 5/053* | (2006.01) | |
| *C08K 5/00* | (2006.01) | |
| *C08L 29/04* | (2006.01) | |
| *A61P 43/00* | (2006.01) | |
| *A61K 9/00* | (2006.01) | |

(52) U.S. Cl.
CPC ............ *A61K 47/26* (2013.01); *A61K 9/0014* (2013.01); *A61K 9/146* (2013.01); *A61K 31/405* (2013.01); *A61P 43/00* (2018.01); *C08K 5/0016* (2013.01); *C08K 5/053* (2013.01); *C08L 29/04* (2013.01)

(58) Field of Classification Search
CPC ...... A61K 47/26; A61K 9/0014; A61K 9/146; A61K 31/405; A61P 43/00; C08K 5/0016; C08K 5/053; C08L 29/04
See application file for complete search history.

(56) References Cited

U.S. PATENT DOCUMENTS 9,814,679 B2  11/2017 Mohammad
2013/0071476 A1* 3/2013 Cherukuri

FOREIGN PATENT DOCUMENTS

| CN | 102204868 A | 10/2011 |
|---|---|---|
| CN | 102204868 B | 1/2014 |
| KR | 20120026595 A | 3/2012 |

OTHER PUBLICATIONS

Aiba et al. (Carbohydrate Polymers, published 1997, pp. 9-19) (Year: 1997).*
Fagron catalog (pp. 1-11, accessed in 2022, https://be.fagron.com/sites/default/files/page/attachment/catalogue_industry.pdf)(Year: 2022).*
Schmidt (Drug Development and Industrial Pharmacy, Published Oct. 2008, p. 2061, Abstract) (Year: 2008).*
International Search Report PCT/EP2017/061126 dated Aug. 3, 2017 (pp. 1-2).
Chiou W. L.; Riegelman S: "Pharmaceutical applications of Solid dispersion systems", J. Pharm Sci., vol. 60, No. 9, 1971, pp. 1281-1301.
Sinswat P. et al.: "Stabilizer choice for rapid dissolving high potency itraconazole particles formed by evaporative precipitation into aqueous solution", Int. J. of Pharmaceutics, vol. 302, 2005, pp. 113-124.
Dinunzio J. C et al.: "Ill Amorphous compositions using concentration enhancing polymers for improved bioavailability of itraconazole", Molecular Pharmaceutics, vol. 5, No. 6, 2008, pp. 968-980.
Breitenbach J.: "Melt extrusion: from process to drug delivery technology", Eur. J. Pharm. Biopharm., vol. 54, 2002, pp. 107-117.
Schilling S. U et al.: "Citric acid as a solid-state plasticizer for Eudragit RS PO", J. Pharm. Pharmacol., vol. 59, No. 11, 2007, pp. 1493-1500.
Michael A. Repka et al.: "Melt extrusion: process to product", Expert Opin. Drug Deliv., vol. 9, No. 1, 2012, pp. 105-125.
Gordon, M.; Taylor, J.S.: "Ideal copolymers and second-order transitions of synthetic rubbers", Journal of Applied Chemistry, vol. 2, 1952, pp. 493-500.
Chamarthy S P et al: "Plasticizer concentration and the performance of a diffusion-controlled polymeric drug delivery system", Colloids and Surfaces A: Physiochemical and Engineering Aspects, Elsevier, Amsterdam, NL, vol. 331, No. 1-2, Dec. 10, 2008 (Dec. 10, 2008), pp. 25-30, XP025680773, ISSN: 0927-7757.
Geert Verreck:;"Hot-Melt Extrusion: Pharmaceutical Applications : Douroumis/Hot-Melt Extrusion: Pharmaceutical Applications", May 25, 2012, John Wiley & Sons, Ltd, Chichester, UK, ISBN: 978-0-470-71118-7, article Geert Verreck: "The Influence of Plasticizers in Hot-Melt Extrusion : Douroumis/Hot-Melt Extrusion: Pharmaceutical Applications", pp. 93-112.

(Continued)

*Primary Examiner* — Alma Pipic
(74) *Attorney, Agent, or Firm* — Millen White Zelano and Branigan, PC; Csaba Henter

(57) ABSTRACT

The present invention relates to the use of spray-dried sorbitol, such as Parteck® SI, as plasticizer for polymer containing compositions processed by (hot) melt extrusion. Due to its improved properties, achieved by its special manufacturing process (spray drying), this direct compressible excipient shows more additional benefits than the same substance in crystalline state.

13 Claims, 5 Drawing Sheets

(56) References Cited

OTHER PUBLICATIONS

DeJaeghere et al: International Journal of Pharmaceutics 492 (2015) 1-9.
English translation of Office Action in corresponding Korean Patent Application No. 10-2018-7036153 dated May 12, 2021. (.

* cited by examiner

HOT MELT EXTRUSION COMPOSITION USING DIRECT COMPRESSIBLE EXCIPIENT AS PLASTICIZER

The present invention relates to the use of spray-dried sorbitol, such as Parteck® SI, as plasticizer for polymer containing compositions processed by (hot) melt extrusion. Due to its improved properties, achieved by its special manufacturing process (spray drying), this direct compressible excipient shows more additional benefits than the same substance in crystalline state.

TECHNICAL FIELD

Solid dispersions are defined as being a dispersion of one or more active ingredients in an inert solid matrix and can broadly classified as those containing a drug substance in the crystalline state or in the amorphous state [Chiou W. L., Riegelman S. Pharmaceutical applications of Solid dispersion systems; J. Pharm Sci. 1971, 60 (9), 1281-1301]. Solid dispersions containing pharmaceutical active ingredients in the crystalline state provide dissolution enhancement by simply decreasing surface tension, reducing agglomeration, and improving wettability of the active substance [Sinswat P., et al.; Stabilizer choice for rapid dissolving high potency itraconazole particles formed by evaporative precipitation into aqueous solution; Int. J. of Pharmaceutics, (2005) 302; 113-124]. While crystalline systems are more thermodynamically stable than their amorphous counterparts, the crystalline structure must be interrupted during the dissolution process, requiring energy. Solid dispersions containing an active ingredient, this means a drug, dissolved at the molecular level, known as amorphous solid solutions, can result in a significant increase in dissolution rate and extent of supersaturation [DiNunzio J. C. et al. III Amorphous compositions using concentration enhancing polymers for improved bioavailability of itraconazole; Molecular Pharmaceutics (2008); 5(6):968-980]. While these systems have several advantages, physical instability can be problematic due to molecular mobility and the tendency of the drug to recrystallize. Polymeric carriers with high glass transition temperatures seem to be well suited to stabilize these systems by limiting molecular mobility.

As such, solid dispersions can be created by a number of methods, including, but not limited to, spray-drying, (hot) melt extrusion, and thermokinetic compounding.

Although hot melt extrusion, a fusion processing technique, has been used in the food and plastics industry for more than a century, it has only recently gained acceptance in the pharmaceutical industry for the preparation of formulations comprising active ingredients processed by extrusion. Nowadays hot melt extrusion (HME) has been introduced as pharmaceutical manufacturing technology and has become a well-known process to formulate solid dispersion with benefits like continuous and effective processing, limited number of process steps, solvent free process etc. During hot melt extrusion mixtures of active ingredients, thermoplastic excipients, and other functional processing aids, are heated and softened or melted inside of an extruder and extruded through nozzles into different forms.

In this method, a thermoplastic carrier may be mixed with a pharmaceutical active substance and optional inert excipients and further additives. The mixture is fed into rotating screws that convey the powder into a heated zone where shear forces are imparted into the mixture, compounding the materials until a molten mass is achieved.

For an amorphous dispersion via melt extrusion, the polymeric carrier vehicle must first possess a thermoplasticity that allows the polymer to be passed through the extruder, and on the other hand the carrier must be thermally stable at barrel temperatures above the glass transition temperature or melting point of the polymer.

During hot melt extrusion the active ingredients are mixed with and embedded in excipients, such as polymers and plasticizers. Furthermore, drug substances are exposed to elevated temperatures for a period of time. Although a variety of factors can affect the residence time distribution of an extruded substance, these times typically fall within the 1- to 2-min range (Breitenbach J., Melt extrusion: from process to drug delivery technology. Eur. J. Pharm. Biopharm. (2002), 54, 107-117).

A prolonged exposure to elevated temperatures can induce decomposition of thermally labile compounds or accelerate decomposition of chemically unstable compounds. But the addition of processing aids, such as plasticizers, may allow processing to be carried out at a lower temperature (Schilling S. U. et al.; Citric acid as a solid-state plasticizer for Eudragit RS PO; J. Pharm. Pharmacol. (2007), 59(11), 1493-1500).

Plasticizers are typically ingredients with relative low molecular weight, either in solid or liquid state, capable of softening of plastic polymers and make the matrix flexible during (hot) melt extrusion processing (Michael A. Repka. et al.; Melt extrusion: process to product; Expert Opin. Drug Deliv. (2012) 9(1), 105-125)). Plasticizers are capable to reduce the glass transition temperature and melt point (crystalline or semi-crystalline polymer) of polymer using for (hot) melt extrusion, during reducing the interaction of polymer chain secondary bonding and provide for more mobility. Plasticizers add free volume of polymer and thereby loosen and local liquid structure of the polymers (Gordon, M. and Taylor, J. S.; Ideal copolymers and second-order transitions of synthetic rubbers. Journal of Applied Chemistry (1952), 2, 493-500). In this case, plasticizers can also decrease the melt viscosity of melted composition, tensile strength, hardness, density and meanwhile increase parameters such as elongation at break, toughness and dielectric constant. Hot melt extrusion is both thermal and mechanical process, these forces and process conditions determine the processability of extrusion and therefore may cause either thermal and mechanical degradation of polymer or active ingredients of the formulation. Therefore, plasticizers play a crucial role of (hot) melt extrusion processing.

The ideal plasticizer should have high compatibility with polymer: mixable with polymer and no re-crystallization after formulation. Additionally, an ideal plasticizer should also be stable under hot melt extrusion condition and sufficiently lubricating and stable in the final product with active ingredients. More important for pharmaceutical application, the plasticizers should compatible for health and safety regulations. Therefore, limited choice of approved plasticizers for pharmaceutical application is available.

Problem to be Solved

For preparation of pharmaceutical formulations in form of solid dispersions it is a common method to homogenize the required ingredients with each other by hot melt extrusion. But because of the already above-described problematic chemical and physical properties of polyvinyl alcohol (PVA), it is difficult to produce corresponding solid compositions comprising PVA as carrier for active ingredients by hot melt extrusion without affecting the active ingredient at the required temperatures and optionally its partial decomposition.

Therefore, it is an object of the present invention to provide a suitable additive, by which the melting point of the entire mixture with a pharmaceutical active ingredient and PVA as a carrier can be lowered to a temperature, which is below the melting point $T_m$ of the applied PVA and which is as low that the active ingredient remains stable during melt extrusion. It is a further object of the present invention to provide a suitable additive, by which the viscosity of the mixture comprising PVA as carrier or excipient for the active ingredient during the extrusion process. It is also an object of the present invention to provide an additive by which the viscosity of said mixture is adjusted during extrusion in a suitable manner.

In addition to this, it is also an object of the present invention to provide a formulation comprising PVA as carrier for an active ingredient and at least an additive in suitable amounts, which shows a melting point $T_m$ below the melting point of the applied PVA and which has a suitable viscosity, such that the comprising active ingredient remains stable during hot melt extrusion and that an extrusion is made possible without any interruption.

Particularly, it is therefore an object of the present invention to provide a composition comprising PVA and an additive, and optionally other ingredients, which allows the formulation of stable homogeneous mixtures in form of solid dispersions containing active ingredients (APIs) and which are processed by hot melt extrusion.

SUMMARY OF THE INVENTION

Unexpectedly it was found by experiments that for the preparation of pharmaceutical formulations the use of low spray-dried sorbitol as plasticizer in polymer containing compositions for hot melt extrusion (HME) or melt extrusion processes is associated with great advantages. Suitable spray-dried sorbitols are commercially available and are selected from the group Parteck® SI 150, Parteck® SI 200, Parteck® SI 400, Parteck® SI 450. The use of these spray-dried sorbitols for the preparation of pharmaceutical formulations containing polymer as carrier matrix is characterized in that the applied polyol reduces the glass transition temperature $T_g$ and the melting temperature $T_m$ of said polymer containing compositions in hot melt extrusion (HME) or melt extrusion processes. Advantageously the applied sorbitol additionally reduces the melting viscosity of the polymer containing thermoplastic composition.

A further advantageous effect is that the use of the spray-dried sorbitol, especially of Parteck® SI stabilizes thermal instable active pharmaceutical ingredients (APIs) and reduces their thermal degradation and acts as solubilisation-enhancer for the applied poorly water-soluble API during hot melt extrusion (HME) or melt extrusion and as stabilizer for the produced amorphous solid dispersion of the API in the polymer matrix during hot melt extrusion (HME) or melt extrusion. Particularly preferred in this context is the use of a spray-dried sorbitol in polyvinyl alcohol (PVA) containing compositions for hot melt extrusion (HME) or melt extrusion processes.

Furthermore, the use of these polyols is particularly advantageous for the preparation of compositions wherein
a) the spray-dried sorbitol is contained in a weight percentage amount in the range of 15-50%,
b) the polymer is contained in a weight percentage amount in the range of 50-85%
and
c) the API is contained in a weight percentage amount in the range of 0.01-40%,
with the proviso that the sum of all ingredients of the composition add up to 100%.

Thus, part of the present invention is also a powdery composition, comprising at least one thermoplastic polymer, and a spray-dried sorbitol as plasticizer, at least one active pharmaceutical ingredient and optionally one or more additives, selected from the group surface active material, anti-oxidant, stabilizing agent, solubility-enhancing agents, pH control agents and flow regulators,
which is obtained by the steps of
a. physical blending or granulating of the ingredients into a homogeneous mixture,
b. hot melt extrusion or melt extrusion
and
c. subsequent confectioning into a powder.

In particular, part of the invention are such powdery compositions comprising polyvinyl alcohol as thermoplastic polymer in combination with a spray-dried sorbitol as plasticizer and at least one active pharmaceutical ingredient.

A particular advantage of this powdery composition is that it is a long-term stable amorphous solid dispersion of at least one active pharmaceutical ingredient in a carrier matrix of a thermoplastic polymer and of spray-dried sorbitol.

The present invention also provides a process for the production of the above powdery compositions according to the invention, characterized in that
a) at least one thermoplastic polymer, a spray-dried sorbitol, at least one active pharmaceutical ingredient and optionally one or more additives, selected from the group surface active material, anti-oxidant, stabilizing agent, solubility-enhancing agents, pH control agents and flow regulators, are processed into a homogeneous mixture by physical blending or granulating, and
b) hot melt extrusion or melt extrusion of this homogeneous mixture is processed, whereby a solid dispersion of the API in the carrier matrix of a thermoplastic polymer and of at least one spray-dried sugar, especially spray-dried sorbitol, is built and
c) that the extrusion product is subsequently confectioned into a powder.

This process is characterized in that polyvinyl alcohol, spray-dried sorbitol and at least one active pharmaceutical ingredient and optionally one or more additives, selected from the group surface active material, anti-oxidant, stabilizing agent, solubility-enhancing agents, pH control agents and flow regulators, are processed into a homogeneous mixture by physical blending or granulating, which is then processed by hot melt extrusion or melt extrusion at a temperature ≤160° C. and confectioned into a powder.

DETAILED DESCRIPTION OF THE INVENTION

The present invention relates to the use of spray-dried sorbitol, such as Parteck® SI, as plasticizer for polymer containing compositions processed by (hot) melt extrusion, in particular for PVA containing formulations. In this context, a substantially improvement of bioavailability and solubility of the drug can be achieved. Additionally, the extrudate formulated with spray-dried sorbitol, such as Parteck® SI, can be milled very easily due to the higher mechanical strength of the extrudate.

Polyvinyl alcohol (PVA) is a synthetic polymer, which is produced by the polymerization of vinyl acetate and partial hydrolysis of the resulting esterified polymer. Chemical and physical properties of PVA (such as viscosity, solubility, thermal properties, etc.) are very depending on its degree of polymerization (chain length of PVA polymer) and the degree of hydrolysis. PVA is useful for different routes of administration to treat a variety of medical conditions and it is used in a wide range of pharmaceutical dosage forms and including ophthalmic, transdermal, topical and especially oral applications.

To manufacture a specific hot melt extrusion dosage form, the active ingredient is embedded in the polymer matrix. The basic requirements for polymers used for HME are: thermoplastic, pharmaceutical grad, suitable glass transition temperature, high thermal stability, no toxicity and high biocompatibility. Therefore, pharmaceutical grade PVAs are chosen to formulate compositions comprising active ingredients and which are produced using hot melt extrusion.

But in general, about 40% of marketed active ingredients and up to 90% of experimental active ingredients has the major problem of poor water solubility. Therefore, it is an object of the present invention to provide a suitable manner and one or more additives for the production of formulations comprising active ingredients from BCS (Biopharmaceutics Classification System) class II and IV with improved solubility in a special polymer matrix. Since extrusion processes are easy to perform in itself compared to other formulation methods, the aim is to solve the above described requirements by hot melt-extruded or melt-extruded formulations.

Thus, a solid pharmaceutical dosage form, which is characterized as disclosed herein and which is obtainable by a process as characterized here, is the subject of the present invention. By making available this solid formulation disadvantages as described above can be overcome in a simple manner.

It is a common method to improve the extrudability of polymer-containing formulations by the addition of plasticizers. Here the expert can choose between various plasticizers that meet the requirements for pharmaceutical formulations and which can be applied in hot melt extrusion technology. The Biopharmaceutics Classification System is a system to differentiate the drugs on the basis of their solubility and permeability. Class I represents high permeability, high solubility drugs; Class II is for the drugs with high permeability, low solubility, for example indomethacin, while Class III is for drugs with low permeability, high solubility and Class IV is for drugs with low permeability, low solubility. Surprisingly, it was found by experiments that, in particular spray-dried sorbitol, such as Parteck® SI, exerts a positive effect on the extrudability of PVA, but at the same time it also improves the solubility of poorly water soluble active agents in the PVA matrix.

But the application of Parteck® SI as plasticizer is not limited to compositions with active ingredients types.

While the making and using of various embodiments of the present invention are discussed in detail below, it should be appreciated that the present invention provides more applicable inventive concepts than described here in detail. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "a homogenous melt, or mixture or form" refers to the various compositions that can be made by extruding the made-up source material, which is prepared by milling and combining selected sieve fractions.

As used herein, the term "heterogeneously homogeneous composite" refers to a material composition having at least two different materials that are evenly and uniformly distributed throughout the volume and which are prepared of the one or more APIs and the one or more pharmaceutically acceptable excipients, including a pretreated PVA into a composite.

As used herein, "bioavailability" is a term meaning the degree to which a drug becomes available to the target tissue after being administered to the body. Poor bioavailability is a significant problem encountered in the development of pharmaceutical compositions, particularly those containing an active ingredient that is not highly soluble.

As used herein, the phrase "pharmaceutically acceptable" refers to molecular entities, compositions, materials, excipients, carriers, and the like that do not produce an allergic or similar untoward reaction when administered to humans in general.

As used herein, "pharmaceutically acceptable carrier" or "pharmaceutically acceptable materials" includes any and all solvents, dispersion media, coatings, antibacterial and antifungal agents, isotonic and absorption delaying agents, and the like. The use of such media and agents for pharmaceutical active substances is well known in the art.

As used herein, the term "plasticizer" includes all compounds capable of plasticizing the applied polymer, preferably polyvinyl alcohol as characterized herein. The plasticizer should be able to lower the glass transition temperature or softening point of the polymer in order to allow for lower processing temperature, extruder torque and pressure during the hot-melt extrusion process. Plasticizers generally broaden the average molecular weight of the polymer thereby lowering its glass transition temperature or softening point. Plasticizers also generally reduce the viscosity of a polymer melt thereby allowing for lower processing temperature and extruder torque during hot-melt extrusion. It is possible that the plasticizer will impart some particularly advantageous physical properties to the produced pharmaceutical formulation.

As used herein, the term "active pharmaceutical ingredient" or "API" means an organic chemical substance having desired beneficial and therapeutic effects in mammals. Such compounds are generally classified as pharmaceuticals or biologicals. As long as the therapeutic compound can diffuse from the formulation when exposed to a biological fluid, its structure is not especially critical.

The API may be found in the form of one or more pharmaceutically acceptable salts, esters, derivatives, analogs, prodrugs, and solvates thereof. As used herein, a "pharmaceutically acceptable salt" is understood to mean a compound formed by the interaction of an acid and a base, the hydrogen atoms of the acid being replaced by the positive ion of the base.

The APIs contemplated within the scope of the invention include hydrophobic, hydrophilic and amphiphilic compounds. They may be in their free acid, free base, or pharmaceutically acceptable salt forms. They may be derivatives or prodrugs of a given pharmaceutical.

It will be appreciated that certain APIs used in the present invention may contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and geometric trans isomers of the therapeutic compounds are described and may be isolated as a mixture of isomers or as separated isomeric forms. All chiral, diastereomeric, racemic forms and all geometric isomeric forms of a structure are intended, unless the specific stereochemistry or isomer form is specifically indicated.

As used herein, "poorly soluble" refers to having a solubility means the substance needs ≥100 ml solvent to dissolve 1 g substance.

It is not necessary for the API to be soluble in any given formulation component. The API may be either dissolved, partially dissolved or suspended in the polymer matrix of the formulation. It is necessary for the API to be stable during the hot-melt extrusion process conditions used. By stable, it is meant that a significant portion of the therapeutic compound will not be significantly degraded or decomposed throughout the hot-melt extrusion process.

As used herein, "derivative" refers to chemically modified inhibitors or stimulators that still retain the desired effect or property of the original API. Such derivatives may be derived by the addition, removal, or substitution of one or more chemical moieties on the parent molecule. Such moieties may include, but are not limited to, an element such as a hydrogen or a halide, or a molecular group such as a methyl group. Such a derivative may be prepared by any method known to those of skill in the art. The properties of such derivatives may be assayed for their desired properties by any means known to those of skill in the art. As used herein, "analogs" include structural equivalents or mimetics.

A variety of administration routes are available for delivering the APIs to a patient in need. The particular route selected will depend upon the particular drug selected, the weight and age of the patient, and the dosage required for therapeutic effect. The pharmaceutical compositions may conveniently be presented in unit dosage form. The APIs suitable for use in accordance with the present disclosure, and their pharmaceutically acceptable salts, derivatives, analogs, prodrugs, and solvates thereof, can be administered alone, but will generally be administered in admixture with a suitable pharmaceutical excipient, diluent, or carrier selected with regard to the intended route of administration and standard pharmaceutical practice.

The APIs may be used in a variety of application modalities, including oral delivery as tablets, capsules or suspensions; pulmonary and nasal delivery; topical delivery as emulsions, ointments or creams; transdermal delivery; and parenteral delivery as suspensions, microemulsions or depot. As used herein, the term "parenteral" includes subcutaneous, intravenous, intramuscular, or infusion routes of administration.

The solution agent used in the solution can be an aqueous such as water, one or more organic solvents, or a combination thereof. The used organic solvents can be water miscible or non-water miscible. Suitable organic solvents may be selected from the group of ethanol, methanol, tetrahydrofuran, acetonitrile, acetone, tert.-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane. But even more solvents may be used here, so that this group is not exhaustive. The solvents can be applied as such or as mixtures thereof.

The excipients and adjuvants, that may be used for the preparation of compositions and composites of the present invention, and which already have certain activities for themselves, like antioxidants, are generally chosen for this application as compounds that enhance the efficiency and/or efficacy of the comprising active ingredients. It is also possible to add more than one effective ingredient to a special solution, which is used in the extrusion process, with the effect that the produced product particles contain more than one effective ingredient. As already noted above, excipients and adjuvants may be used to enhance the efficacy and efficiency of APIs in formulations.

Compositions and composites, prepared according to the present invention may also comprise thermal binders and may also be formulated to exhibit enhanced dissolution rate of a formulated poorly water soluble drug.

Depending on the desired administration form the formulations can be designed to be suitable in different release models, which are well known to the skilled person, as there are: immediate, rapid or extended release, delayed release or for controlled release, slow release dosage form or mixed release, including two or more release profiles for one or more active pharmaceutical ingredients, timed release dosage form, targeted release dosage form, pulsatile release dosage form, or other release forms.

The APIs, which may be hot-melt extruded in the formulation of the invention, may be used for treating indications such as, by way of example and without limitation, inflammation, gout, hypercholesterolemia, microbial infection, AIDS, tuberculosis, fungal infection, amoebic infection, parasitic infection, cancer, tumor, organ rejection, diabetes, heart failure, arthritis, asthma, pain, congestion, urinary tract infections, vaginal infection, seizure related disorder, depression, psychosis, convulsion, diabetes, blood coagulation, hypertension and birth control.

Loading of the APIs into the final formulation may be accomplished following the techniques below. Generally, the therapeutic compound is loaded by premixing it with the polyvinyl alcohol and any other formulation components and hot-melt extruding the mixture. When solids are present in the mixture, they may be, by way of example and without limitation, either powdered, crystalline, amorphous, pelletized, beaded, spheronized, granular or the like.

It should be understood that the amount of API loaded into the formulation may be varied according to, for example, the polymer: API or the polymer: plasticizer: API ratios used in the pre-extruded mixture. Although a given loading method may be optimal for a particular polyvinyl alcohol: API combination, all of the described methods will generally result in API loading to some degree.

The therapeutic amount of API loaded into the formulation will vary according to the pharmacological activity of the API, the indication being treated, the targeted dosing regimen, the projected method of administration, the integrity or stability of the final formulation or other such reasons.

The United States Pharmacopeia-National Formulary mandates that an acceptable polyvinyl alcohol for use in pharmaceutical dosage forms must have a percentage of hydrolysis between 85 and 89%, as well as a degree of polymerization between 500 and 5000. The degree of polymerization (DM) is calculated by the equation:

$$DM = (\text{Molar Mass}) / ((86) - (0.42 (\text{the degree of hydrolysis})))$$

The European Pharmacopoeia mandates that an acceptable polyvinyl alcohol for use in pharmaceutical dosage forms must have an ester value no greater than 280 and a mean relative molecular mass between 20,000 and 150,000. The percentage of hydrolysis (H) can be calculated from the following equation:

$$H=((100-(0.1535)(EV))/(100-(0.0749)(EV)))\times 100$$

Where EV is the ester value of the polymer. Thus, only polymers with a percentage of hydrolysis greater than 72.2% are acceptable according to the European Pharmacopoeia monograph.

As already mentioned above, commercial polyvinyl alcohols in particulate form have poor flow behavior, especially if they are characterized by low viscosities (measured in a 4% aqueous solution at 20° C.). Accordingly, these powders have no continuous trouble-free flow. However, the latter is a prerequisite for a uniform feed to the processing of such powder materials.

Theoretically, powders, whose particle shapes are rather round and spherical, in general have the best flow behavior. Accordingly, in the past, attempts have been made to produce polyvinyl alcohol powders already directly by its synthesis with spherical particles. For example, from DE 38 11 201A a method is known for producing of spherical particles by suspension polymerization. However, this reaction requires a special adjustment of the reaction conditions. In addition, this reaction has to be followed by a hydrolysis reaction. With different particle sizes, it is difficult to achieve a uniform degree of hydrolysis of the polymer particles. By this method, polyvinyl alcohol powders are produced having viscosities of 80 mPa·s or higher.

Therefore, for the production of polyvinyl alcohol powders, which are comparable with those of the present invention, this method provides no alternative, especially as here PVA grades are desirable having viscosities of ≤40 mPa·s.

Now, it was found that these polyvinyl alcohol grades having viscosities of ≤40 mPa·s are also suitable to be manufactured by melt extrusion if they are pretreated as disclosed in the following and a homogenously dispersed solid solution of pharmaceutical active ingredient in polyvinyl alcohol can be produced by extrusion and the applied PVA powder can be fed without problems into the feeder.

In this way also poorly soluble pharmaceutical active ingredients (from BCS class II and IV) can be homogeneously mixed with PVA to build a solid dispersion. Furthermore, it was found by experiments that PVA in the different degrees of hydrolysis having viscosities of ≤40 mPa·s can be homogeneously mixed by melt extrusion with poorly soluble active ingredients, especially with PVA that is in accordance with the European Pharmacopoeia monograph and which is a pharmaceutically acceptable PVA with hydrolysis grades greater than 72.2%, and especially which includes grades of PVA that are pharmaceutically acceptable by either the USP (hydrolysis between 85-89%) or Ph. Eur. (hydrolysis grades greater than 72.2%). These PVA qualities have a molecular weight in the range of 14,000 g/mol to 250,000 g/mol.

Powdery compositions according to the invention may comprise at least a biologically active ingredient combined with a PVA that is pharmaceutically acceptable, which is combined with another pharmaceutically acceptable polymer. Such pharmaceutically acceptable polymer can also be selected from the group of hydrophilic polymers and can be a primary or secondary polymeric carrier that can be included in the composition disclosed herein and including polyethylene-polypropylene glycol (e.g. POLOXAMER™), carbomer, polycarbophil, or chitosan, provided that they are as free-flowing powder and is extrudable polymers. Hydrophilic polymers for use with the present invention may also include one or more of hydroxypropyl methylcellulose, carboxymethylcellulose, hydroxypropyl cellulose, hydroxyethyl cellulose, methylcellulose, natural gums such as gum guar, gum acacia, gum tragacanth, or gum xanthan, and povidone. Hydrophilic polymers also include polyethylene oxide, sodium carboxymethycellulose, hydroxyethyl methyl cellulose, hydroxymethyl cellulose, carboxypolymethylene, polyethylene glycol, alginic acid, gelatin, polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

In general, it must be considered that there are special requirements for polymers used as hot melt extrusion excipients:

The polymer must be thermoplastic, and must have a suitable glass transition temperature and a high thermal stability. The polymer must have no toxic properties and must have a high biocompatibility, etc. Therefore, pharmaceutical grades of polyvinyl alcohol (PVA), which are chosen here for the preparation of formulations comprising active ingredients by hot melt extrusion, are those having a low viscosity.

Polyvinyl alcohol (PVA) is a synthetic polymer, which is produced by the polymerization of vinyl acetate and partial hydrolysis of the resulting esterified polymer. As already mentioned above, chemical and physical properties of polyvinyl alcohol, such as viscosity, solubility, thermal properties, etc. are very depending on its degree of polymerization, chain length of PVA polymer, and the degree of hydrolysis.

PVA can be used for the production of different formulations for various modes of administration to treat a variety of disorders. Accordingly, PVA is processed in a wide range of pharmaceutical dosage forms, including ophthalmic, transdermal, topical, and especially, oral application forms.

As used herein, the term "hot-melt extrudable" refers to a compound or formulation that may be hot-melt extruded. A hot-melt extrudable polymer is one that is sufficiently rigid at standard ambient temperature and pressure but is capable of deformation or forming a semi-liquid state under elevated heat or pressure.

Although the process referred to has been called a hot-melt extrusion, other equivalents processes may be used. By using any of these methods, the formulation may be shaped as needed according to the desired mode of administration, e.g. tablets, pills, lozenges, suppositories and the like.

The hot-melt extrusion process employed in some embodiments of the invention is conducted at an elevated temperature, i.e. the heating zone(s) of the extruder is above room temperature (about 20° C.). It is important to select an operating temperature range that will minimize the degradation or decomposition of the active pharmaceutical compound during processing. The operating temperature range is generally in the range of from about 60° C. to about 160° C. as determined by the following experiments and by the setting for the extruder heating zone(s). These experiments have shown, that the operating temperature can be set at temperatures ≤160° C.

In a preferred embodiment of the invention, the hot-melt extrusion can be conducted employing a solid, powdered or other such feed comprising polyvinyl alcohol, spray-dried sorbitol and an active ingredient and optionally further compounds. Dry feed is advantageously employed in the process of the present invention.

The hot-melt extrusion process is generally described as follows. An effective amount of a powdered API is mixed with a suitable polymer acting as carrier matrix, and as disclosed here, with a plasticizer such as spray-dried sorbitol. Other components may be added in the various embodiments of the invention.

In the inventive embodiments of the present invention, it has proven to be advantageous when
a) the spray-dried sorbitol, preferably Parteck® SI is contained in the composition in a weight percentage amount in the range of 15-50%,
b) the polymer, preferably PVA, is contained in a weight percentage amount in the range of 50-85% and
c) the API is contained in a weight percentage amount in the range of 0.01-40%,
with the proviso that the sum of all ingredients of the composition add up to 100%,
depending on the desired release profile, the pharmacological activity and toxicity of the selected active pharmaceutical ingredient and other such considerations. The mixture is then placed in the extruder feeder and passed through the heated area of the extruder at a temperature which will melt or soften the polymer and plasticizer, to form a matrix throughout which the active ingredient is homogeneously dispersed. The molten or softened mixture then exits via a die, or other such element, at which time, the mixture (now called the extrudate) begins to harden. Since the extrudate is still warm or hot upon exiting the die, it may be easily shaped, molded, chopped, ground, molded, spheronized into beads, cut into strands, tableted or otherwise processed to the desired physical form. Preferably, the extrudate is confectioned to a powdery composition.

The extruder used to practice the invention may be any such commercially available model equipped to handle dry feed and having a solid conveying zone, one or multiple heating zones, and an extrusion die. A two stage single screw extruder is one such apparatus. It is particularly advantageous for the extruder to possess multiple separate temperature controllable heating zones.

Many conditions may be varied during the extrusion process to arrive at a particularly advantageous formulation. Such conditions include, by way of example, formulation composition, feed rate, operating temperature, extruder screw RPM, residence time, die configuration, heating zone length and extruder torque and/or pressure. Methods for the optimization of such conditions are known to the skilled artisan.

As mentioned above, for the successful industrial processing of a solid in an extrusion process it is also necessary that a uniform continuous metering is possible in the feed of the extruder.

The experiments have shown, that for this purpose, the solid must have suitable particle characteristics, including appropriate particle sizes, and flowability or fluidity.

It was also found through the experiments, that by the inventive pretreatment of appropriate commercially available PVA optionally by blending with suitable ingredients a stable product is obtained, which may be prepared as a ready-to-use product. Such a product can easily be loaded into the feeder of the extruder without any interruption and it makes the extrusion process feasible although a PVA is used as an excipient having a low viscosity of ≤40 mPa·s.

It was found, that an easily extrudable product can be obtained, when a commercially available PVA with pharma grade and low viscosity of ≤40 mPa·s is milled into fine powder and blended with ingredients.

The resulting mixture can be fed continuously without problems and without any halt into the feeder of an extruder. Thus, the pretreatment of the applied PVA makes, that the extrusion process is feasible in a simple manner. In addition, it has been found, that not only the milling to a fine powder improves the uniform feeding of the PVA powder into the feeder of the extruder. Surprisingly, further significant improvement in the flowability of the milled polymer powder is achieved by sieving the milled polymer into various sieve fractions, and subsequent combining certain sieve fractions having specific grain sizes with each other. In summary, clearly defined particle sizes and size distributions result in PVA powders with significantly improved flowability and thus in an improved processability of the received PVA powders.

Surprisingly it was found by experiments for the preparation of pharmaceutical formulations, that spray-dried sorbitol, such as Parteck® SI, is outstandingly suitable as plasticizer for formulations for hot melt extrusion which contain PVA as polymer matrix for the active ingredient. This is unexpected since spray-dried sorbitol itself is useful as a directly compressible carrier for the preparation of pharmaceutical formulations in tablet form, whereas crystalline sorbitol is problematic in this context. The above Parteck SI® is commercially available from Merck Millipore, Darmstadt. The experiments have shown, that spray-dried sorbitol or Parteck® SI can increase the solubility of ingredients more effective and make the extrudate more stable. Additionally, the extrudate formulated with PVA as polymer matrix is easy to be milled due to the higher mechanical strength of extrudate.

For pharmaceutical applications of hot melt extrusion, plasticizers are added to the composition and formulated with active ingredients and other additional functional excipients into a final dosage form, which is usually tablet, capsule, pellets or polymeric film. In this context, Parteck® SI, a direct compression excipient, is an excellent plasticizer for (hot) melt extrusion compared with normal crystalline sorbitol. Parteck® SI is a directly compressible sorbitol for solid dosage preparation, which is produced using a unique spray drying technology. It consists of just one component, sorbitol, and is free of additional binder. Its unique and very large surface area creates excellent compressibility and adsorption of active ingredients and supports good content uniformity even with low dose formulations. As direct compression excipient Parteck® SI has the benefits such as high compactability, large and highly structured surface area, fast disintegration etc. Parteck® SI, excipient EMPROVE® exp Ph Eur, USP, JPE, Merck KGaA, Darmstadt, Germany:
Parteck® SI 150 Article No. 103583
Parteck® SI 200 Article No. 115079
Parteck® SI 400 Article No. 103140
Parteck® SI 400 LEX Article No. 111597
Parteck® SI 450 Article No. 103557

The processed experiments are carried out using Parteck® SI as spray-dried sorbitol and as plasticizer to reduce the melt viscosity and $T_g$ and $T_m$ of polyvinyl alcohol. This direct compressible excipient is chosen because of its improved properties due to its special manufacturing process (spray drying). This direct compressible excipient is suitable as plasticizer and reduces the glass transition temperature and melting point of polymer effectively. Parteck® SI shows more additional benefits than the same substance in crystalline state which is not produced using spray drying:
1. higher enhancement of ingredient solubility
2. enhancement of long-term stability of the produced extrudate
3. no recrystallization of plasticizer after long-term storage 4. better mechanical strength of extrudate, which is important for milling/grinding of extrudate
5. improved flowability of the (hot) melt extrusion composition.

EXAMPLES

Even without any further explanations, it is assumed that a person skilled in the art can make use of the above description in its widest scope. The preferred embodiments and examples are therefore to be regarded merely as descriptive but in no way limiting disclosures.

For better understanding and for illustration, examples are given below which are within the scope of protection of the present invention. These examples also serve for the illustration of possible variants.

The complete disclosure of all applications, patents and publications mentioned above and below are incorporated by reference in the present application and shall serve in cases of doubt for clarification.

It goes without saying that, both in the examples given and also in the remainder of the description, the quoted percentage data of the components present in the compositions always add up to a total of 100% and not more. Given temperatures are measured in ° C.

Methods and Materials
1. Raw Materials and Manufacturing Method
1.1 Materials
Raw Materials:
Parteck® SI 150, Article No. 103583, excipient EMPROVE® exp Ph Eur, USP, JPE, Merck KGaA, Darmstadt, Deutschland:
Sorbogem 834 (crystalline sorbitol), Product code 10111, PI Pharma,
Polyvinyl alcohol 4-88, excipient EMPROVE® exp Ph Eur, USP, JPE, Article No. 1.41350, Merck KGaA, Darmstadt, Deutschland
Indomethacin, active ingredient, Sigma, 17378-100G
1.2 Equipment for Experiments & Analysis
Instrument for Angle of repose DIN ISO 4324
    Stirrer (not always necessary)
    Glass Funnel
    Device for closing or opening the output of the funnel (flap)
    Transparent plastic receptacle (diameter 10 cm)
    Measuring block (to measure the cone of the powder)
    Stand with disk
    Spirit level
Different sizes of sieves
Extruder: Brabender® Mini-Compounder KETSE 12/36 D)
Physical blend of composition for hot melt extrusion, including active ingredients: TURBULA® Shaker-Mixer
Miller to grand the extrudate in powder: IKA®M 20 Universalmill
Brabender® Pelletizer
Dissolution experiment:
    Sotax AT 7 on/offline
    Pump CY-7-50/Pump CP 7-35
    C613 14 Channel 3-way valve bar for test tubes
    Agilent 8453 Photometer
    Photometer Analytic Jena Specord 200 plus
Differential scanning calorimetry (DSC)
    TA Instruments Q2000 Differential Scanning Calorimeter
1.3 Experiments and Characterization Methods
1.3.1 Hot Melt Extrusion and Extrudability
At first, mixture of plasticizer, polymer and active ingredient were blended using TURBULA® Shaker-Mixer homogeneously (the concentration of polymer and active ingredient depends on the types and physical properties of them). The mixture was then loaded into the extruder with well designed extrusion parameters, such as feeding rate, screw design, screw speed, extrusion temperature etc. The set up of those parameters depend also on the types and physical properties of polymer and active ingredients. For the extrusion of PVA alone with 30% indomethacin we used following hot melt extrusion processing parameters:
Temperature setting: 80° C./200° C./200° C./200° C./200° C.
Screw speed: 170 rpm
Loading rate of composition: 170 g/h
For the extrusion of PVA with Parteck® SI as plasticizer and 30% additional indomethacin, we used following hot melt extrusion processing parameters:
Temperature setting: 80° C./160° C./160° C./160° C./160° C.
Screw speed: 170 rpm
Loading rate of composition: 170 g/h
For the extrusion of PVA with Sorbogem 834 (crystalline sorbitol) as plasticizer and 30% additional indomethacin, we used following hot melt extrusion processing parameters:
Temperature setting: 80° C./160° C./160° C./160° C./160° C.
Screw speed: 170 rpm
Loading rate of composition: 170 g/h
1.3.2 Milling of Extrudate
The obtained extrudate will be micronized into fine particle (<1000 μm) using a universal miller.
1.3.3 Dissolution
For the real time dissolution performance, we used following equipments:
System 1:
Sotax AT 7 on/offline
Pump CY-7-50
C613 14 Channel 3-way valve bar for test tubes
Agilent 8453 Photometer
System 2
Sotax AT 7 on/offline
Pump CP 7-35
C 613 14 Channel 3-way valve bar for test tubes
Photometer Analytic Jena Specord 200 plus
1.3.4 Differential Scanning Calorimetry
Min. temperature: −20° C.
Max. temperature: 150° C.
Heating Rate: 10K/min
1.3.5 Payload of Active Ingredient (Concentration of API)
The concentration of active ingredient of extrudate was detected by NMR spectroscopy, to evaluate if there was any thermal or mechanical degradation of active ingredient or not.

Determination of Indomethacin Content by NMR Spectroscopy

For determination of the indomethacin content about 20 mg of sample and 20 mg of maleic acid are exactly weighted and dissolved in DMSO-d6. The clear solution is transferred into a 5 mm NMR tube. The 1H-NMR spectra are recorded on a 500 MHz Bruker Avance III spectrometer equipped with a cryo-cooled TCI probe. The FID is digitzed by 128 k data points over a spectral width of 25 ppm. A total of 32 spectra are accumulated with a relaxation delay of 10 s between each scan. Prior to the Fourier transformation, the recorded FID is multiplied with an exponential function (lb=0.3 Hz). The phase and the baseline is corrected for the obtained spectrum.

For calculation of the Indomethacin content the resonance of the CH protons of maleic acid (ca. 6.3 ppm) and the CH protons of Indomethacin (e.g. 6.7 ppm, 6.9 ppm or 7.0 ppm) are integrated. The integral of maleic acid is set to 100. The content is calculated according to the general formula:

$$w_x[\%] = w_{St}[\%] \cdot \frac{z_{St} M_x I_x m_{St}}{z_x M_{St} I_{St} m_x}$$

$w_{St}$ [%]=content of standard in %

$z_{St}$=number of protons of standard contributing to the signal $M_x$=molar mass of the compound of interest x $I_x$=integral of the signal of the compound of interest x $m_{St}$=weighted mass of the standard $z_x$=number of protons of the compound of interest x contributing to the signal $M_{St}$=molar mass of the standard $I_{St}$=integral of the signal of the standard $m_x$=weighted mass of the compound of interest x FIG. 1: shows a NMR spectrogram of 20 mg indomethacin and 20 mg maleic acid in DMSO-d6 1.4.6 Long term stability of extrudate Extrudate with PVA (matrix), sorbitol (plasticizer) and indomethacin (active ingredient) was milled into fine particle and stored under the condition 25° C./60% in a closed vessel for at least 6 months. Samples after long term storage will be analyzed if there was any recrystallization of active ingredient or plasticizer.

2. Research Results 2.1 Physical Characterization of Plasticizer

We characterized the physical properties of Parteck® SI and crystalline sorbitol and compared them regarding their efficiency as plasticizer for (hot) melt extrusion.

2.1.1 Flowability

FIG. 2: Flowability of PVA powder with different sorbitol types 2.1.2 DSC

FIG. 3: Differential scanning calorimetry (DSC) of Parteck® SI and crystalline sorbitol 2.1.3 REM FIG. 4: Rasterelektronenmikroskop of Parteck® SI and crystalline sorbitol 2.1.4 Appearance of Extrudate

TABLE 1

Physical properties of extrudate based on different sorbitol types

| Samples | Mechanical strength of extrudate | Transparency of extrudate |
|---|---|---|
| Extrudate with 75% PVA and 25% Parteck ® SI as plasticizer | Hard/brittle | transparent |
| Extrudate with 75% PVA and 25% crystalline sorbitol as plasticizer | elastic | Slightly turbid |

TABLE 2

Relation between sorbitol concentration and HME processing temperature

| Composition | HME Processing Temp. [° C.] | Extrudate |
|---|---|---|
| PVA without sorbitol | 190 | Transparent |
| PVA/spray dried sorbito1 = 5/1 | 160 | Transparent |
| PVA/spray dried sorbito1 = 4/1 | 150-160 | Transparent |
| PVA/spray dried sorbito1 = 3/1 | 150 | Transparent |
| PVA/spray dried sorbito1 = 2/1 | 140-150 | Transparent |
| PVA/spray dried sorbito1 = 1/1 | 140 | Transparent |

2.2 Solubility improvement of API (Dissolution)

FIG. 5: Real time dissolution of indomethacin with extrudate of PVA/Parteck® SI and PVA/crystalline sorbitol 2.3 Long Term Stability of Extrudate After 6 months storage under condition 25° C./60% we used DSC to check if there was recrystallization of sorbitol or not.

FIG. 6: DSC of extrudate PVA/Parteck® SI/Indomethacin after 6 months storage under 25° C./60%

FIG. 7: DSC of extrudate PVA/crystalline sorbitol/Indomethacin after 6 months storage under 25° C./60%: recrystalline peak of sorbitol was observed after 6 months (in the red circle: recrystallization of sorbitol was observed after 6 months)

2.4 Summary of the Results

During our research work we fund several significant benefits of Parteck® SI as hot melt extrusion plasticizer, in comparison with normal crystalline sorbitol:

More enhancement of active ingredient solubility (real time dissolution results of indomethacin)

Enhancement of extrudate long term stability: no recrystallization of active ingredients and Parteck® SI itself Better mechanical strength of extrudate: Tg of Parteck® SI is higher than crystalline sorbitol, advantage for long term stability and milling of extrudate Flowability enhancement of co-excipients for hot melt extrusion

Figure 1:
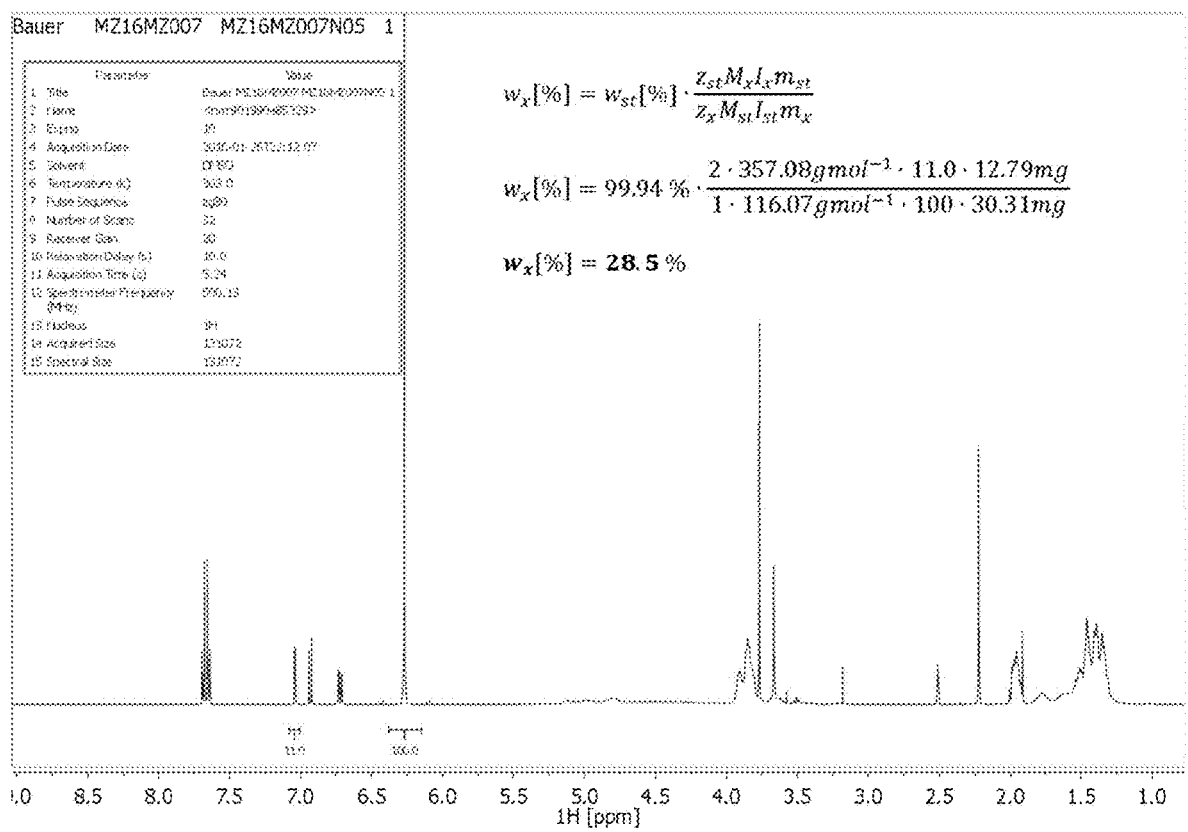
FIGS. 1-3 and 5-7 are graphs
Figure 2:
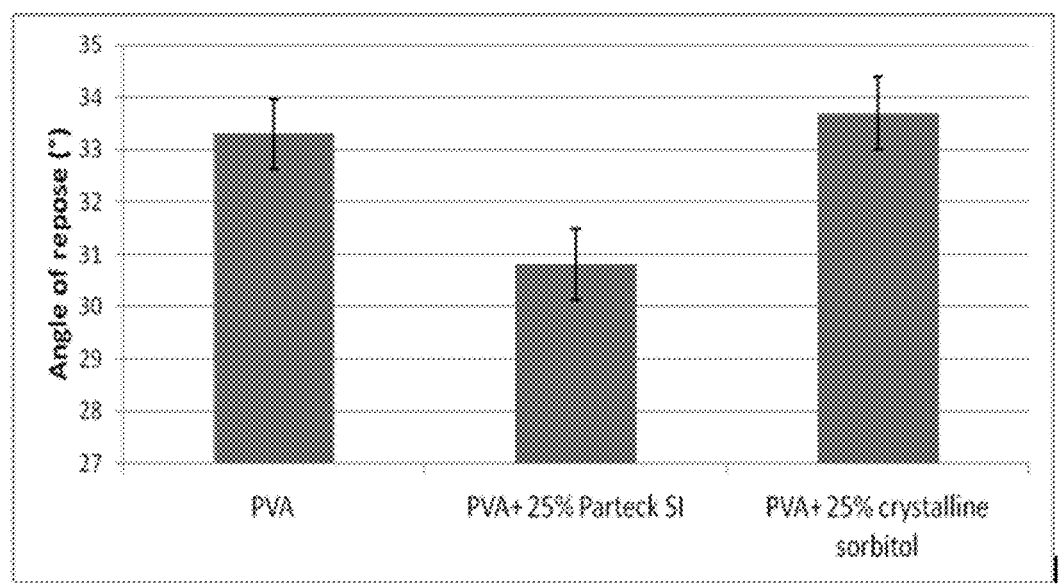
Figure 3:
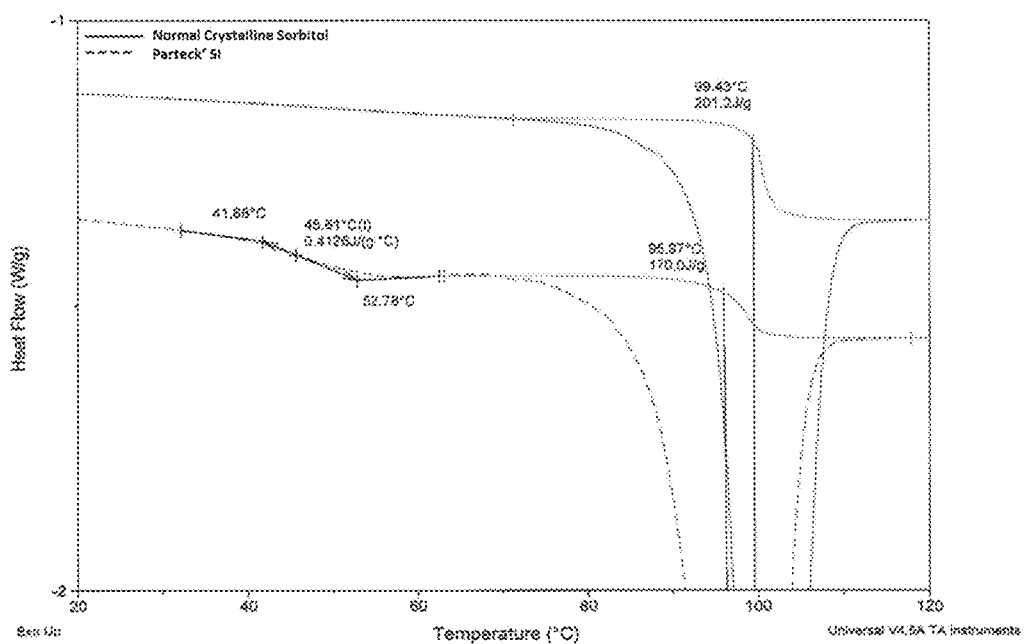
Figure 4:
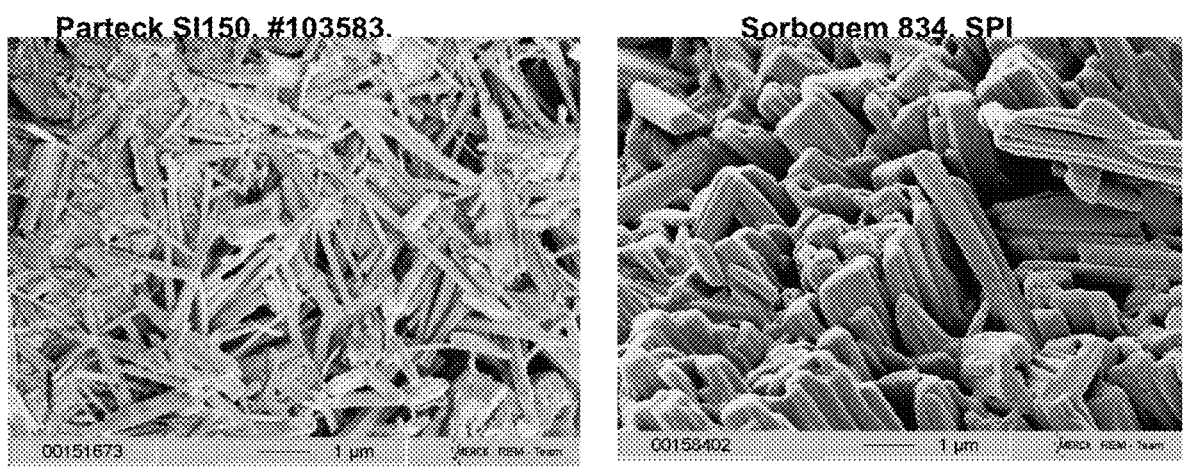
FIG. 4 comprises two photographs
Figure 5:
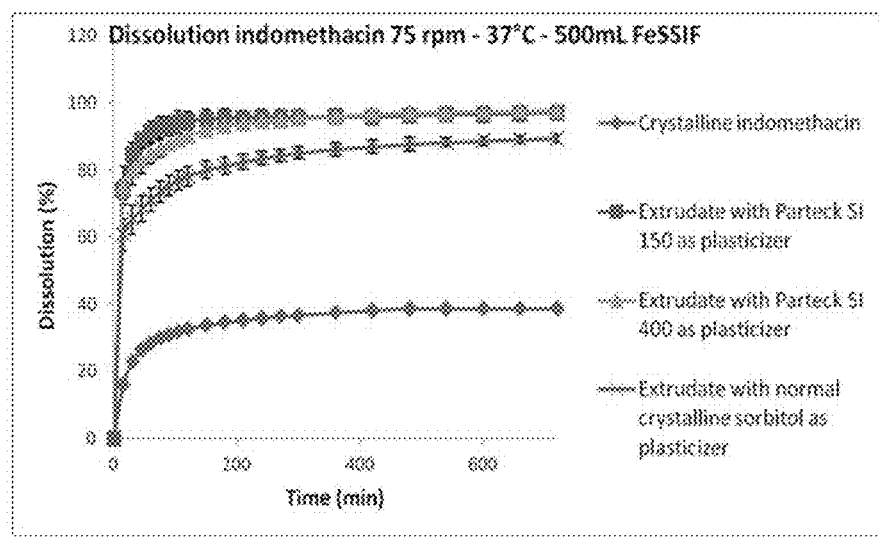
Figure 6:
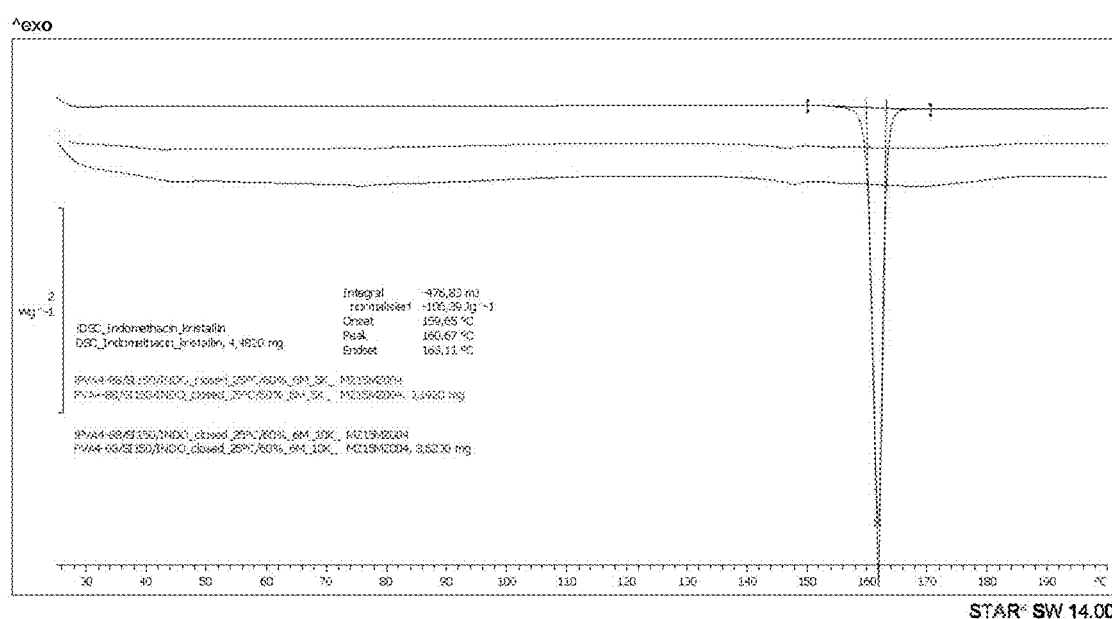
Figure 7:
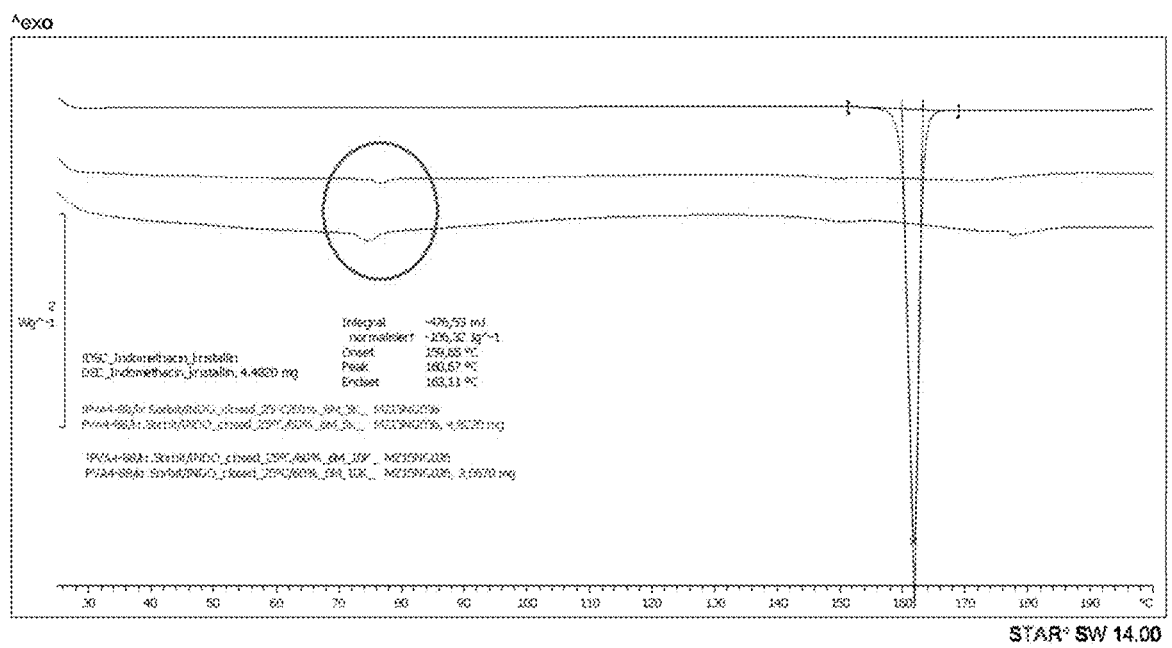

What is claimed is:

1. A hot melt extrusion or melt extrusion process comprising
    plasticizing a composition comprising polyvinyl alcohol with a spray-dried sorbitol by combining the composition comprising polyvinyl alcohol with the spray-dried sorbitol to form a mixture, and
    hot melt extruding or melt extruding the mixture by melting and extruding.

2. The method according to claim 1, wherein the spray-dried sorbitol reduces the glass transition temperature $T_g$ and the melting temperature $T_m$ of the composition comprising polyvinyl alcohol.

3. The method according to claim 1, wherein the spray-dried sorbitol reduces the melting viscosity of the composition comprising polyvinyl alcohol.

4. The method according to claim 1, wherein the composition comprising polyvinyl alcohol further comprises a thermally unstable active pharmaceutical ingredient, and wherein the spray-dried sorbitol stabilizes the thermally unstable active pharmaceutical ingredient and reduces thermal degradation of the thermally unstable active pharmaceutical ingredient.

5. The method according to claim 1,
wherein the composition comprising polyvinyl alcohol further comprises an active pharmaceutical ingredient, wherein the hot melt extruding or melt extruding forms an amorphous solid dispersion of the active pharmaceutical ingredient, and
wherein the spray-dried sorbitol acts as a solubilization-enhancer for said active pharmaceutical ingredient and as a stabilizer for the amorphous solid dispersion of the active pharmaceutical ingredient.

6. The method according to claim 1, wherein the composition comprising polyvinyl alcohol further comprises an active pharmaceutical ingredient, and wherein the mixture comprises
 a) 15-50 wt. % of the spray-dried sorbitol,
 b) 50-85 wt. % of polyvinyl alcohol, and
 c) 0.01-40 wt. % of the active pharmaceutical ingredient,
 with the proviso that all ingredients add up to 100%.

7. The method according to claim 1, wherein the composition comprising polyvinyl alcohol optionally further comprises
one or more additives selected from the group consisting of surface active materials, anti-oxidants, stabilizing agents, solubility-enhancing agents, pH control agents and flow regulators,
wherein the method further comprises physically blending or granulating the mixture into a homogeneous mixture,
hot melt extruding or melt extruding by melting and extruding the homogeneous mixture to form an extrusion product, and
confectioning the extrusion product into a powder.

8. A method of making a pharmaceutical composition comprising a solid active pharmaceutical ingredient, where the solid active pharmaceutical ingredient is in the form of an amorphous solid dispersion, the method comprising
plasticizing a composition comprising polyvinyl alcohol and the solid active pharmaceutical ingredient with a solid spray-dried sorbitol by combining the composition comprising polyvinyl alcohol and the solid active pharmaceutical ingredient with the solid spray-dried sorbitol to form a mixture,
and
hot melt extruding or melt extruding the mixture by melting and extruding.

9. The method according to claim 8, wherein the composition comprising polyvinyl alcohol and the solid active pharmaceutical ingredient
optionally further comprises one or more additives selected from the group consisting of surface active materials, anti-oxidants, stabilizing agents, solubility-enhancing agents, pH control agents and flow regulators,
and wherein the method further comprises physical blending or granulating the mixture to form a homogeneous mixture,
hot melt extruding or melt extruding the homogeneous mixture to form an extrusion product, and
confectioning the extrusion product into a powder.

10. The method according to claim 9, wherein the powder comprises a stable amorphous solid dispersion of the solid active pharmaceutical ingredient, and wherein the polyvinyl alcohol and the spray-dried sorbitol form a carrier matrix for the stable amorphous solid dispersion.

11. The method according to claim 8, wherein the composition comprising polyvinyl alcohol and the solid active pharmaceutical ingredient
optionally further comprises one or more additives selected from the group consisting of surface active materials, anti-oxidants, stabilizing agents, solubility-enhancing agents, pH control agents and flow regulators,
wherein the method further comprises physically blending or granulating the mixture to form a homogeneous mixture,
hot melt extruding or melt extruding by melting and extruding the homogeneous mixture to form an extrusion product,
wherein the extrusions product comprises an amorphous solid dispersion of the solid active pharmaceutical ingredient is-formed in a carrier matrix, wherein the carrier matrix is formed from the polyvinyl alcohol and the solid spray-dried sorbitol, and
confectioning the extrusion product into a powder.

12. The method according to claim 11, wherein hot melt extruding or melt extruding is performed at a temperature ≤160° C.

13. The method according to claim 8, wherein the pharmaceutical composition comprises
 a) 15-50 wt. % of the solid spray-dried sorbitol,
 b) 50-85 wt. % of polyvinyl alcohol, and
 c) 0.01-40 wt. % of the solid active pharmaceutical ingredient,
 with the proviso that all ingredients add up to 100%.

* * * * *